US010220068B2

(12) United States Patent
Heller et al.

(10) Patent No.: US 10,220,068 B2
(45) Date of Patent: Mar. 5, 2019

(54) PHYTONUTRIENT COMPOSITIONS AND METHODS TO PROTECT AGAINST RADICAL MEDIATED CELLULAR AND DNA DAMAGE

(71) Applicant: Metaproteomics, LLC, San Clemente, CA (US)

(72) Inventors: Andrea Lyra Heller, Gig Harbor, WA (US); Brian Carroll, Gig Harbor, WA (US); Matthew L. Tripp, Gig Harbor, WA (US); Jeffrey S. Bland, Fox Island, WA (US)

(73) Assignee: METAPROTEOMICS, LLC, Aliso Viejo, CA (US)

( * ) Notice: Subject to any disclaimer, the term of this patent is extended or adjusted under 35 U.S.C. 154(b) by 164 days.

(21) Appl. No.: 13/715,794

(22) Filed: Dec. 14, 2012

(65) Prior Publication Data
US 2013/0156870 A1    Jun. 20, 2013

Related U.S. Application Data (60) Provisional application No. 61/576,158, filed on Dec. 15, 2011.

(51) Int. Cl.
| | |
|---|---|
| *A61K 36/87* | (2006.01) |
| *A61K 31/353* | (2006.01) |
| *A61K 31/216* | (2006.01) |
| *A61K 31/366* | (2006.01) |
| *A61K 31/7048* | (2006.01) |
| *A61K 36/736* | (2006.01) |
| *A61K 36/45* | (2006.01) |
| *A61K 36/48* | (2006.01) |
| *A61K 36/28* | (2006.01) |
| *A61K 36/54* | (2006.01) |
| *A61K 36/42* | (2006.01) |
| *A61K 36/53* | (2006.01) |
| *A61K 36/31* | (2006.01) |
| *A61K 31/192* | (2006.01) |

(52) U.S. Cl.
CPC ............ *A61K 36/87* (2013.01); *A61K 31/192* (2013.01); *A61K 31/216* (2013.01); *A61K 31/353* (2013.01); *A61K 31/366* (2013.01); *A61K 31/7048* (2013.01); *A61K 36/28* (2013.01); *A61K 36/31* (2013.01); *A61K 36/42* (2013.01); *A61K 36/45* (2013.01); *A61K 36/48* (2013.01); *A61K 36/53* (2013.01); *A61K 36/54* (2013.01); *A61K 36/736* (2013.01)

(58) Field of Classification Search
None
See application file for complete search history.

(56) References Cited

U.S. PATENT DOCUMENTS

| | | |
|---|---|---|
| 2003/0180395 A1 | 9/2003 | Bueter |
| 2008/0089941 A1 | 4/2008 | Mower |
| 2010/0112099 A1 | 5/2010 | Tripp et al. |
| 2011/0159121 A1 | 6/2011 | McDaniel |
| 2011/0300227 A1* | 12/2011 | Danhof .......................... 424/523 |
| 2013/0156870 A1 | 6/2013 | Heller et al. |

FOREIGN PATENT DOCUMENTS

WO      2013/090715 A1    6/2013

OTHER PUBLICATIONS

Singh et al., Antioxidant and anti-quorum sensing activities of green pod of Acacia nilotica L, 2009, Food and Chemical Toxicology, 47: 778-786.*
Park et al., 2007, Researchgate, Antioxidant Activity of Momordica charantia L. Extracts, https://www.researchgate.net/publication/264017829_Antioxidant_Activity_of_Momordica_charantia_L_Extracts.*
Jayaprakasha et al., Antioxidant activity of grape seed (*Vitis vinifera*) extracts on perioxidation models in vitro, 2001, Food Chemistry, 73: 285-290).*
Kayano et al., Antioxidant Activity of Prune (*Prunus domestica* L.) Constituents and a New Synergist, 2002, J Agric food Chem, 50: 3708-3712.*
Mancini-Filho et al., Antioxidant activity of cinnamon (*Cinnamomum zeylanicum*, Breyne) extracts, 1998, Boll Chim Farm, 137: 443-7.*
Wilmsen et al., Antioxidant Activity of the Flavonoid Hesperidin in Chemical and Biological Systems, 2005, J Agric Food Chem, 53: 4757-4761.*
Farah et al., Chlorogenic Acids from Green Coffee Extract are Highly Bioavailable in Humans, 2008, J Nutr, 138: 2309-2315.*
Antioxidant in Berries and Other Fruits 2010 (http://web.archive.org/web/20100103153332/http://www.webmd.com/diet/features/antioxidantsinfruits?).*
Menghini et al., Antiproliferative, protective and antioxidant effects of artichoke, dandelion, turmeric and rosemary extracts and their formulation, 2010, Int J Immunopathol Pharmacol, 23: 601-10.*
Search Report issued in International Patent Application No. PCT/US12/69739 dated Feb. 28, 2013.
International Preliminary Examination Report issued in PCT/US2013/041600 dated Nov. 18, 2014.
International Preliminary Report on Patentability issued in International Application No. PCT/US2012/069739 dated Jun. 17, 2014.
U.S. Office Action issued in related U.S. Appl. No. 13/897,080, dated Jun. 19, 2015; 23 pages.
Revilla et al. Comparison of Several Procedures Used for the Extraction of Anthocynains From Red Grapes; J. Agric. Food Chem. 1998, 46, pp. 4592-4597.
Phillipson, J. New Drugs From Nature—It Could Be Yew; Phytotherapy Research 13 (1999) pp. 2-8.

(Continued)

*Primary Examiner* — Terry A McKelvey
*Assistant Examiner* — Catheryne Chen
(74) *Attorney, Agent, or Firm* — Warner Norcross & Judd LLP (57) ABSTRACT

Phytonutrient based compositions and methods of using the same for preventing, reducing, or treating genetic damage induced by environmental toxins are disclosed.

18 Claims, 6 Drawing Sheets

(56) References Cited

OTHER PUBLICATIONS

H.B. MacPhillamy: Drugs From Plants; Plant Science Bulletin, Botanical Society of America, vol. 9, No. 2, Apr. 1963.
Raskin et al. Can an Apple a Day Keep the Doctor Away? Current Pharmaceutical Design, 2004, 10, 3419-3429.
Lu, Hongmei, et al. (2006) "Variation in Chemical Composition and Antibacterial Activities of Essential Oils From Two Species of Houttuynia Thunb." Chem. Pharm. Bull. vol. 54, No. 7, pp. 936-940.
U.S. Final Office Action issued in related U.S. Appl. No. 13/897,080, dated Mar. 21, 2016.

* cited by examiner

Tail Moment: OG5495

| Tail Moment | n | Mean | 75% CI | SE | SD |
|---|---|---|---|---|---|
| DMSO Control | 372 | 1.036 | 0.882 to 1.190 | 0.1339 | 2.5831 |
| 100 ug/ml OG5495 | 269 | 10.100 | 9.360 to 10.840 | 0.6419 | 10.5277 |
| 20 uM H2O2 | 245 | 37.711 | 36.914 to 38.508 | 0.6911 | 10.8177 |
| 0 uM H2O2 + 100 ug/ml OG5495 | 232 | 26.977 | 26.023 to 27.931 | 0.8275 | 12.6037 |
| 20 uM H2O2 + 20 ug/ml OG5495 | 195 | 39.873 | 38.979 to 40.767 | 0.7745 | 10.8148 |
| 2 uM H2O2 | 194 | 3.246 | 2.646 to 3.846 | 0.5198 | 7.2398 |
| 2 uM H2O2 + 100 ug/ml OG5495 | 149 | 15.292 | 14.152 to 16.432 | 0.9873 | 12.0514 |
| 2 uM H2O2 + 20 ug/ml OG5495 | 213 | 5.269 | 4.699 to 5.839 | 0.4941 | 7.2108 |

| Tail Moment | n | Min | Median | 75% CI | Max |
|---|---|---|---|---|---|
| DMSO Control | 372 | 0.00 | 0.000 | 0.000 to 0.000 | 33.31 |
| 100 ug/ml OG5495 | 269 | 0.00 | 7.430 | 6.570 to 8.140 | 49.02 |
| 20 uM H2O2 | 245 | 0.00 | 39.820 | 39.260 to 40.670 | 59.67 |
| 0 uM H2O2 + 100 ug/ml OG5495 | 232 | 0.00 | 26.075 | 23.920 to 27.030 | 52.45 |
| 20 uM H2O2 + 20 ug/ml OG5495 | 195 | 0.00 | 41.240 | 40.690 to 42.070 | 62.45 |
| 2 uM H2O2 | 194 | 0.00 | 0.085 | 0.000 to 0.450 | 76.86 |
| 2 uM H2O2 + 100 ug/ml OG5495 | 149 | 0.00 | 13.900 | 11.380 to 15.180 | 55.49 |
| 2 uM H2O2 + 20 ug/ml OG5495 | 213 | 0.00 | 1.480 | 0.880 to 2.420 | 38.16 |

Fig. 1

%DNA in Tail: OG5495

| %DNA in Tail | n | Mean | 75% CI | SE | SD |
|---|---|---|---|---|---|
| DMSO Control | 372 | 3.675 | 3.216 to 4.134 | 0.3984 | 7.6834 |
| 100 ug/ml OG5495 | 269 | 32.575 | 30.787 to 34.362 | 1.5504 | 25.4285 |
| 20 uM H2O2 | 245 | 88.516 | 87.391 to 89.641 | 0.9758 | 15.2730 |
| 0 uM H2O2 + 100 ug/ml OG5495 | 232 | 72.152 | 70.626 to 73.678 | 1.3232 | 20.1539 |
| 20 uM H2O2 + 20 ug/ml OG5495 | 195 | 92.273 | 90.878 to 93.668 | 1.2091 | 16.8845 |
| 2 uM H2O2 | 194 | 11.859 | 10.394 to 13.324 | 1.2698 | 17.6861 |
| 2 uM H2O2 + 100 ug/ml OG5495 | 149 | 48.524 | 46.045 to 51.003 | 2.1467 | 26.2040 |
| 2 uM H2O2 + 20 ug/ml OG5495 | 213 | 18.808 | 17.139 to 20.478 | 1.4474 | 21.1243 |

| %DNA in Tail | n | Min | Median | 75% CI | Max |
|---|---|---|---|---|---|
| DMSO Control | 372 | 0.00 | 0.045 | 0.020 to 0.070 | 80.76 |
| 100 ug/ml OG5495 | 269 | 0.00 | 30.750 | 26.910 to 32.440 | 98.96 |
| 20 uM H2O2 | 245 | 0.00 | 94.150 | 93.520 to 94.740 | 99.75 |
| 0 uM H2O2 + 100 ug/ml OG5495 | 232 | 0.00 | 74.400 | 72.360 to 77.010 | 99.90 |
| 20 uM H2O2 + 20 ug/ml OG5495 | 195 | 0.00 | 97.440 | 97.120 to 97.740 | 99.95 |
| 2 uM H2O2 | 194 | 0.00 | 2.205 | 0.310 to 4.700 | 95.55 |
| 2 uM H2O2 + 100 ug/ml OG5495 | 149 | 0.00 | 48.930 | 46.150 to 52.710 | 99.41 |
| 2 uM H2O2 + 20 ug/ml OG5495 | 213 | 0.00 | 11.770 | 8.710 to 15.180 | 86.49 |

Fig. 2

Tail Moment: OG5507

| Tail Moment | n | Mean | 75% CI | SE | SD |
|---|---|---|---|---|---|
| DMSO Control | 285 | 0.714 | 0.610 to 0.819 | 0.0907 | 1.5314 |
| 100 ug/ml OG5507 | 196 | 2.332 | 2.060 to 2.603 | 0.2352 | 3.2932 |
| 20 uM H2O2 | 183 | 22.708 | 21.697 to 23.720 | 0.8767 | 11.8599 |
| 0 uM H2O2 + 100 ug/ml OG5507 | 210 | 3.080 | 2.675 to 3.486 | 0.3516 | 5.0945 |
| 20 uM H2O2 + 20 ug/ml OG5507 | 206 | 16.826 | 16.037 to 17.614 | 0.6837 | 9.8126 |
| 2 uM H2O2 | 266 | 1.566 | 1.301 to 1.831 | 0.2296 | 3.7444 |
| 2 uM H2O2 + 100 ug/ml OG5507 | 204 | 1.690 | 1.430 to 1.950 | 0.2254 | 3.2190 |
| 2 uM H2O2 + 20 ug/ml OG5507 | 210 | 2.237 | 1.796 to 2.677 | 0.3821 | 5.5373 |

| Tail Moment | n | Min | Median | 75% CI | Max |
|---|---|---|---|---|---|
| DMSO Control | 285 | 0.00 | 0.000 | 0.000 to 0.000 | 12.39 |
| 100 ug/ml OG5507 | 196 | 0.00 | 0.935 | 0.490 to 1.450 | 26.39 |
| 20 uM H2O2 | 183 | 0.00 | 20.410 | 19.580 to 21.880 | 58.43 |
| 0 uM H2O2 + 100 ug/ml OG5507 | 210 | 0.00 | 0.660 | 0.390 to 1.020 | 42.14 |
| 20 uM H2O2 + 20 ug/ml OG5507 | 206 | 0.00 | 15.715 | 15.300 to 16.600 | 51.01 |
| 2 uM H2O2 | 266 | 0.00 | 0.000 | 0.000 to 0.030 | 43.14 |
| 2 uM H2O2 + 100 ug/ml OG5507 | 204 | 0.00 | 0.180 | 0.070 to 0.320 | 28.20 |
| 2 uM H2O2 + 20 ug/ml OG5507 | 210 | 0.00 | 0.050 | 0.000 to 0.180 | 47.27 |

Fig. 3

%DNA in Tail: OG5507

| %DNA in Tail | n | Mean | 75% CI | SE | SD |
|---|---|---|---|---|---|
| DMSO Control | 285 | 3.131 | 2.726 to 3.536 | 0.3516 | 5.9359 |
| 100 ug/ml OG5507 | 196 | 9.516 | 8.643 to 10.389 | 0.7567 | 10.5935 |
| 20 uM H2O2 | 183 | 64.132 | 62.489 to 65.774 | 1.4235 | 19.2569 |
| 0 uM H2O2 + 100 ug/ml OG5507 | 210 | 11.153 | 10.093 to 12.214 | 0.9195 | 13.3244 |
| 20 uM H2O2 + 20 ug/ml OG5507 | 206 | 52.831 | 51.316 to 54.346 | 1.3132 | 18.8479 |
| 2 uM H2O2 | 266 | 5.918 | 5.202 to 6.634 | 0.6209 | 10.1267 |
| 2 uM H2O2 + 100 ug/ml OG5507 | 204 | 7.211 | 6.373 to 8.049 | 0.7262 | 10.3721 |
| 2 uM H2O2 + 20 ug/ml OG5507 | 210 | 7.402 | 6.256 to 8.547 | 0.9927 | 14.3851 |

| %DNA in Tail | n | Min | Median | 75% CI | Max |
|---|---|---|---|---|---|
| DMSO Control | 285 | 0.00 | 0.080 | 0.050 to 0.140 | 46.46 |
| 100 ug/ml OG5507 | 196 | 0.00 | 6.220 | 4.260 to 8.130 | 68.77 |
| 20 uM H2O2 | 183 | 0.00 | 64.720 | 63.900 to 66.750 | 98.96 |
| 0 uM H2O2 + 100 ug/ml OG5507 | 210 | 0.00 | 6.620 | 5.070 to 8.340 | 96.84 |
| 20 uM H2O2 + 20 ug/ml OG5507 | 206 | 0.00 | 54.800 | 53.500 to 55.880 | 94.02 |
| 2 uM H2O2 | 266 | 0.00 | 0.340 | 0.120 to 1.530 | 85.49 |
| 2 uM H2O2 + 100 ug/ml OG5507 | 204 | 0.00 | 3.155 | 1.690 to 4.190 | 69.62 |
| 2 uM H2O2 + 20 ug/ml OG5507 | 210 | 0.00 | 1.230 | 0.750 to 1.920 | 92.88 |

PHYTONUTRIENT COMPOSITIONS AND METHODS TO PROTECT AGAINST RADICAL MEDIATED CELLULAR AND DNA DAMAGE

CROSS-REFERENCE TO RELATED APPLICATIONS

This patent application claims priority to U.S. provisional application Ser. No. 61/576,158, filed on Dec. 15, 2011, the entire content of which is hereby incorporated herein by reference in its entirety as though fully set forth herein.

BACKGROUND OF THE INVENTION

Field of the Invention

The present invention relates to phytonutrient compositions and methods of using the same for preventing, reducing, or treating genetic damage induced by environmental agents.

Description of the Related Art

A consequence of our modern industrial society has been the proliferation of chemicals and agents released into the environment having the capacity to induce genetic damage. The list of such chemicals and agents is extensive and grows at an ever increasing pace. Some examples of these agents include heavy metals, PCBs, pesticides, volatile organic compounds, phthalates, chlorine, dioxins, chloroform, and asbestos. Modern building methods stressing air tightness and energy efficiency have now made molds a problematic concern.

The list of offending compounds grows daily, in large part, due to recent advances and enhanced sensitivity in detecting DNA damage caused by such environmental agents. This is especially true where assays are now conducted at the individual cell level.

DNA damage can occur naturally and is usually repaired via natural repair processes in the body. It is when the rate of damage exceeds the body's ability to keep up with repairs that health problems ensue. Some health problems associated with environmental toxin exposure include liver and kidney damage (chloroform), mesotheilioma (asbestos), reproductive damage (dioxins), and nerve damage (pesticides). Additionally, some disorders including cerebral palsy, ADHD, epilepsy, and Tourette syndrome have been ascribed to fetal exposure to various chemicals.

As the list of offending agents increases, one questions whether any lifestyle changes in today's society can alleviate the risks entirely. Today, this seems an unlikely scenario as many of the offending agents have become integral to our way of life. What is therefore needed are means to prevent DNA damage from occurring initially or, alternatively, reduce or correct the damage subsequent to damage initiation to prevent the accumulation of DNA damage from reaching a level of health concerns.

The inventors disclose phytonutrient based compositions and methods which may be used to prevent, treat, or reduce DNA damage at the cellular level due to exposure to environmental toxins.

SUMMARY OF THE INVENTION

The present invention relates to phytonutrient compositions and methods of using the same for preventing, reducing, or treating genetic damage induced by environmental agents.

A first embodiment of the invention describes phytonutrient compositions for preventing, reducing, or treating genetic damage induced by environmental agents, where the compositions comprise therapeutically effective amounts of two or more compounds selected from the group consisting of *Acacia nilotica* extract, artichoke extract, blueberry extract, catechins, chlorogenic acid, cinnamon, ellagic acid, grape seed extract, hesperidin, *Momordica* extract, prune extract, rosemary extract, and watercress extract and the composition is in a dosage form suitable for oral administration.

A second embodiment of the invention describes methods for preventing, reducing, or treating genetic damage induced by environmental agents, where the methods comprise administering a composition comprising therapeutically effective amounts of two or more compounds selected from the group consisting of *Acacia nilotica* extract, artichoke extract, blueberry extract, catechins, chlorogenic acid, cinnamon, ellagic acid, grape seed extract, hesperidin, *Momordica* extract, prune extract, rosemary extract, and watercress extract and the composition is in a dosage form suitable for oral administration.

DETAILED DESCRIPTION OF THE INVENTION

The present invention relates to phytonutrient compositions and methods of using the same for preventing, reducing, or treating genetic damage induced by environmental agents.

The patents, published applications, and scientific literature referred to herein establish the knowledge of those with skill in the art and are hereby incorporated by reference in their entirety to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of recombinant DNA technology include Sambrook et al., Molecular Cloning: A Laboratory Manual, 2nd Ed., Cold Spring Harbor Laboratory Press, New York (1989); Kaufman et al., Eds., Handbook of Molecular and Cellular Methods in Biology in Medicine, CRC Press, Boca Raton (1995); McPherson, Ed., Directed Mutagenesis: A Practical Approach, IRL Press, Oxford (1991). Standard reference works setting forth the general principles of pharmacology include Goodman and Gilman's The Pharmacological Basis of Therapeutics, 11th Ed., McGraw Hill Companies Inc., New York (2006).

In the specification and the appended claims, the singular forms include plural referents unless the context clearly dictates otherwise. As used in this specification, the singular forms "a," "an" and "the" specifically also encompass the plural forms of the terms to which they refer, unless the content clearly dictates otherwise. Additionally, as used herein, unless specifically indicated otherwise, the word "or" is used in the "inclusive" sense of "and/or" and not the "exclusive" sense of "either/or." The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

As used herein, the recitation of a numerical range for a variable is intended to convey that the invention may be practiced with the variable equal to any of the values within that range. Thus, for a variable that is inherently discrete, the variable can be equal to any integer value of the numerical range, including the end-points of the range. Similarly, for a variable that is inherently continuous, the variable can be equal to any real value of the numerical range, including the end-points of the range. As an example, a variable that is described as having values between 0 and 2, can be 0, 1 or 2 for variables that are inherently discrete, and can be 0.0, 0.1, 0.01, 0.001, or any other real value for variables that are inherently continuous.

Reference is made hereinafter in detail to specific embodiments of the invention. While the invention will be described in conjunction with these specific embodiments, it will be understood that it is not intended to limit the invention to such specific embodiments. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known process operations have not been described in detail, in order not to unnecessarily obscure the present invention.

A first embodiment of the invention describes phytonutrient compositions for preventing, reducing, or treating genetic damage induced by environmental agents, where the compositions comprise therapeutically effective amounts of two or more compounds selected from the group consisting of *Acacia nilotica* extract, artichoke extract, blueberry extract, catechins, chlorogenic acid, cinnamon, ellagic acid, grape seed extract, hesperidin, *Momordica* extract, prune extract, rosemary extract, and watercress extract and the composition is in a dosage form suitable for oral administration.

In an aspect of this embodiment, the composition provides per dosage form:
a. from 0.5 mg to 10 mg of *Acacia nilotica* extract;
b. from 0.5 mg to 10 mg of artichoke extract;
c. from 1 mg to 25 mg of blueberry extract;
d. from 2.5 mg to 25 mg of catechins;
e. from 25 mg to 75 mg of chlorogenic acid;
f. from 0.5 mg to 10 mg of cinnamon;
g. from 10 mg to 100 mg of ellagic acid;
h. from 2.5 mg to 50 mg of grape seed extract;
i. from 15 mg to 120 mg of hesperidin;
j. from 0.5 mg to 10 mg of *Momordica* extract;
k. from 0.5 mg to 10 mg of prune extract;
l. from 0.5 mg to 10 mg of rosemary extract; and
m. from 0.5 mg to 10 mg of watercress extract.

As used herein, a "phytonutrient" refers to nutrients derived from plant materials shown to be necessary for sustaining human life. Encompassed within phytonutrients are "phytochemicals", that is, plant derived compounds not yet classified as substances needed for sustaining life yet known to have properties useful for aiding in the prevention of disease.

As used herein, "genetic damage" refers to damage to the cell's DNA (either physical or in the sense of its information capacity) when it mutates (or deviates) from its original form. There are many known substances which can damage DNA, such as, for example, oxidizing agents, alkylating agents and electromagnetic radiation. Damage by these agents includes cross linking between the pyrimidine bases, base modifications and double strand breaks.

As used herein, the term "extract" refers to the solid material resulting from exposing a plant material to a solvent, (2) separating the solvent from the plant material, and eliminating the solvent.

As used herein, the term "solvent" refers to a liquid of aqueous or organic nature possessing the necessary characteristics to extract solid material from plant material. Examples of solvents would include water, steam, superheated water, methanol, ethanol, hexane, chloroform, liquid $CO_2$, liquid $N_2$ or any combinations of such materials.

The term "acacia", as used herein, refers to any member of leguminous trees and shrubs of the genus *Acacia*. Preferably, the botanical compound derived from *acacia* is derived from *Acacia catechu* or *Acacia nilotica*. In those aspects where the *acacia* derived compound or extract is derived from *Acacia catechu* or *Acacia nilotica*, the *Acacia catechu* or *Acacia nilotica* compound is selected from the group consisting of gum resin, bark powder, heartwood powder, and an *Acacia catechu* or *Acacia nilotica* extract. In those aspects where the *acacia* derived compound is an *Acacia catechu* or *Acacia nilotica* extract, the extract is selected from acidic, alkaline, polar solvent, nonpolar solvent, and gastric fluid extracts.

As used herein, by "treating" is meant reducing, preventing, and/or reversing the symptoms in the individual to which a compound of the invention has been administered, as compared to the symptoms of an individual not being treated according to the invention. A practitioner will appreciate that the compounds, compositions, and methods described herein are to be used in concomitance with continuous clinical evaluations by a skilled practitioner (physician or veterinarian) to determine subsequent therapy. Hence, following treatment the practitioners will evaluate any improvement in the treatment of the pulmonary inflammation according to standard methodologies. Such evaluation will aid and inform in evaluating whether to increase, reduce or continue a particular treatment dose, mode of administration, etc.

It will be understood that the subject to which a compound of the invention is administered need not suffer from a specific traumatic state. Indeed, the compounds of the invention may be administered prophylactically, prior to any development of symptoms. The term "therapeutic," "therapeutically," and permutations of these terms are used to encompass therapeutic, palliative as well as prophylactic uses. Hence, as used herein, by "treating or alleviating the symptoms" is meant reducing, preventing, and/or reversing the symptoms of the individual to which a compound of the invention has been administered, as compared to the symptoms of an individual receiving no such administration.

The term "therapeutically effective amount" is used to denote treatments at dosages effective to achieve the therapeutic result sought. Furthermore, one of skill will appreciate that the therapeutically effective amount of the compound of the invention may be lowered or increased by fine tuning and/or by administering more than one compound of the invention, or by administering a compound of the invention with another compound. See, for example, Meiner, C. L., "Clinical Trials: Design, Conduct, and Analysis," Monographs in Epidemiology and Biostatistics, Vol. 8 Oxford University Press, USA (1986). The invention therefore provides a method to tailor the administration/treatment to the particular exigencies specific to a given mammal. As illustrated in the following examples, therapeutically effective amounts may be easily determined for example empirically by starting at relatively low amounts and by step-wise increments with concurrent evaluation of beneficial effect.

It will be appreciated by those of skill in the art that the number of administrations of the compounds according to the invention will vary from patient to patient based on the particular medical status of that patient at any given time including other clinical factors such as age, weight and condition of the mammal and the route of administration chosen.

As used herein, "compounds" may be identified either by their chemical structure, chemical name, or common name. When the chemical structure and chemical or common name conflict, the chemical structure is determinative of the identity of the compound. The compounds described herein may contain one or more chiral centers and/or double bonds and therefore, may exist as stereoisomers, such as double-bond isomers (i.e., geometric isomers), enantiomers or diastereomers. Accordingly, the chemical structures depicted herein encompass all possible enantiomers and stereoisomers of the illustrated or identified compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds may also exist in several tautomeric forms including the enol form, the keto form and mixtures thereof. Accordingly, the chemical structures depicted herein encompass all possible tautomeric forms of the illustrated or identified compounds. The compounds described also encompass isotopically labeled compounds where one or more atoms have an atomic mass different from the atomic mass conventionally found in nature. Examples of isotopes that may be incorporated into the compounds of the invention include, but are not limited to, $^2H$, $^3H$, $^{13}C$, $^{14}C$, $^{15}N$, $^{18}O$, $^{17}O$, etc. Compounds may exist in unsolvated forms as well as solvated forms, including hydrated forms and as N-oxides. In general, compounds may be hydrated, solvated or N-oxides. Certain compounds may exist in multiple crystalline or amorphous forms. Also contemplated within the scope of the invention are congeners, analogs, hydrolysis products, metabolites and precursor or prodrugs of the compound. In general, unless otherwise indicated, all physical forms are equivalent for the uses contemplated herein and are intended to be within the scope of the present invention.

Compounds according to the invention may be present as salts. In particular, pharmaceutically acceptable salts of the compounds are contemplated. A "pharmaceutically acceptable salt" of the invention is a combination of a compound of the invention and either an acid or a base that forms a salt (such as, for example, the magnesium salt, denoted herein as "Mg" or "Mag") with the compound and is tolerated by a subject under therapeutic conditions. In general, a pharmaceutically acceptable salt of a compound of the invention will have a therapeutic index (the ratio of the lowest toxic dose to the lowest therapeutically effective dose) of 1 or greater. The person skilled in the art will recognize that the lowest therapeutically effective dose will vary from subject to subject and from indication to indication, and will thus adjust accordingly.

The compounds according to the invention are optionally formulated in a pharmaceutically acceptable vehicle with any of the well known pharmaceutically acceptable carriers, including diluents and excipients [see Remington's Pharmaceutical Sciences, 18th Ed., Gennaro, Mack Publishing Co., Easton, Pa. 1990 and Remington: The Science and Practice of Pharmacy, Lippincott, Williams & Wilkins, 1995]. While the type of pharmaceutically acceptable carrier/vehicle employed in generating the compositions of the invention will vary depending upon the mode of administration of the composition to a mammal, generally pharmaceutically acceptable carriers are physiologically inert and non-toxic. Formulations of compositions according to the invention may contain more than one type of compound of the invention), as well as any other pharmacologically active ingredient useful for the treatment of the symptom/condition being treated.

The compounds of the present invention may be provided in a pharmaceutically acceptable vehicle using formulation methods known to those of ordinary skill in the art. The compositions of the invention can be administered by standard routes, though preferably administration is by inhalation routes. The compositions of the invention include those suitable for oral, inhalation, rectal, ophthalmic (including intravitreal or intracameral), nasal, topical (including buccal and sublingual), vaginal, or parenteral (including subcutaneous, intramuscular, intravenous, intradermal, and intratracheal). In addition, polymers may be added according to standard methodologies in the art for sustained release of a given compound.

Formulations suitable for administration by inhalation include formulations that can be dispensed by inhalation devices known to those in the art. Such formulations may include carriers such as powders and aerosols. The present invention encompasses liquid and powdered compositions suitable for nebulization and intrabronchial use, or aerosol compositions administered via an aerosol unit dispensing metered doses ("MDI"). The active ingredient may be formulated in an aqueous pharmaceutically acceptable inhalant vehicle, such as, for example, isotonic saline or bacteriostatic water and other types of vehicles that are well known in the art. The solutions are administered by means of a pump or squeeze-actuated nebulized spray dispenser, or by any other conventional means for causing or enabling the requisite dosage amount of the liquid composition to be inhaled into the patient's lungs. Powder compositions containing the anti-inflammatory compounds of the present invention include, by way of illustration, pharmaceutically acceptable powdered preparations of the active ingredient thoroughly intermixed with lactose or other inert powders acceptable for intrabronchial administration. The powder compositions can be administered via a dispenser, including, but not limited to, an aerosol dispenser or encased in a breakable capsule which may be inserted by the patient into a device that punctures the capsule and blows the powder out in a steady stream. Aerosol formulations for use in the subject method typically include propellants, surfactants, and co-solvents and may be filled into conventional aerosol containers that are closed by a suitable metering valve.

Formulations of compositions of the present invention suitable for nasal administration, wherein the carrier is a solid, include a coarse powder having a particle size, for example, in the range of 20 to 500 microns which is administered in the manner in which snuff is administered, i.e., by rapid inhalation through the nasal passage from a container of the powder held close up to the nose. Suitable formulations, wherein the carrier is a liquid, for administration, for example via a nasal spray, aerosol, or as nasal drops, include aqueous or oily solutions of the compound of the invention.

For oral administration, the compositions of the invention may be presented as discrete units such as capsules, caplets, gelcaps, cachets, pills, or tablets each containing a predetermined amount of the active ingredient as a powder or granules; as a solution or a suspension in an aqueous liquid or a non-aqueous liquid; or as an oil-in-water liquid emulsion or a water-in-oil emulsion and as a bolus, etc. Alternately, administration of a composition of all of the aspects of the present invention may be effected by liquid solutions, suspensions or elixirs, powders, lozenges, micronized particles and osmotic delivery systems.

Formulations of compositions according to the aspects of the present invention suitable for parenteral administration include aqueous and non-aqueous sterile injection solutions which may contain antioxidants, stabilizers, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze-dried (lyophilized) conditions requiring only the addition of the sterile liquid carrier, for example, water for injections, immediately prior to use. Extemporaneous injection solutions and suspensions may be prepared from sterile powders, granules and tablets of the kind previously described.

A tablet may be made by compression or molding, optionally with one or more accessory ingredients. Compressed tablets may be prepared by compressing, in a suitable machine, the active ingredient in a free-flowing form such as a powder or granules, optionally mixed with a binder, lubricant, inert diluent, preservative, surface active or dispersing agent. Molded tablets may be made by molding, in a suitable machine, a mixture of the powdered compound moistened with an inert liquid diluent. The tablets may be optionally coated or scored and may be formulated to provide a slow or controlled release of the active ingredient therein.

Formulations of compositions of the present invention for rectal administration may be prepared as a suppository with a suitable base comprising, such as, for example, cocoa butter.

Formulations of compositions of the present invention suitable for topical administration in the mouth include lozenges comprising the ingredients in a flavored basis, usually sucrose and *acacia* or tragacanth; pastilles comprising the active ingredient in an inert basis such as gelatin and glycerin, or sucrose and *acacia*; and mouthwashes comprising the ingredient to be administered in a suitable liquid carrier. Formulations of compositions of the present invention suitable for topical administration to the skin may be presented as ointments, creams, gels, lotions and pastes comprising the ingredient to be administered in a pharmaceutical acceptable carrier. A topical delivery system contemplated is a transdermal patch containing the ingredient to be administered.

Formulations of compositions according to the aspects of the present invention suitable for vaginal administration may be presented as pessaries, suppositories, tampons, creams, gels, pastes, foams or spray formulations containing in addition to the compound of the invention such pharmaceutically acceptable carriers as are known in the art to be appropriate.

The methods and compositions of the present invention are intended for use with any mammal that may experience the benefits of the methods of the invention. Foremost among such mammals are humans, although the invention is not intended to be so limited, and is applicable to veterinary uses. Thus, in accordance with the invention, "mammals" or "mammal in need" include humans as well as non-human mammals, particularly domesticated animals including, without limitation, cats, dogs, and horses.

A second embodiment of the invention describes methods for preventing, reducing, or treating genetic damage induced by environmental agents, where the methods comprise administering a composition comprising therapeutically effective amounts of two or more compounds selected from the group consisting of *Acacia nilotica* extract, artichoke extract, blueberry extract, catechins, chlorogenic acid, cinnamon, ellagic acid, grape seed extract, hesperidin, *Momordica* extract, prune extract, rosemary extract, and watercress extract and the composition is in a dosage form suitable for oral administration.

In an aspect of this embodiment, the composition of the method provides per dosage form:
   a. from 0.5 mg to 10 mg of *Acacia nilotica* extract;
   b. from 0.5 mg to 10 mg of artichoke extract;
   c. from 1 mg to 25 mg of blueberry extract;
   d. from 2.5 mg to 25 mg of catechins;
   e. from 25 mg to 75 mg of chlorogenic acid;
   f. from 0.5 mg to 10 mg of cinnamon;
   g. from 10 mg to 100 mg of ellagic acid;
   h. from 2.5 mg to 50 mg of grape seed extract;
   i. from 15 mg to 120 mg of hesperidin;
   j. from 0.5 mg to 10 mg of *Momordica* extract;
   k. from 0.5 mg to 10 mg of prune extract;
   l. from 0.5 mg to 10 mg of rosemary extract; and
   m. from 0.5 mg to 10 mg of watercress extract.

Any suitable materials and/or methods known to those of skill can be utilized in carrying out the present invention. However, preferred materials and methods are described. Materials, reagents and the like to which reference are made in the following description and examples are obtainable from commercial sources, unless otherwise noted.

EXAMPLES

Example 1

Effects of Compositions OG5495 and OG5507 on Healthy and Hydrogen Peroxide Treated Jurkat Cells By CometAssay Purpose:

To evaluate effects of test compositions OG5495 and OG5507 on healthy and hydrogen peroxide treated Jurkat cells by CometAssay. The formulations for compositions OG5495 and OG5507 are presented in Table 1 below.

TABLE 1

| Ingredient | OG5507 (mg/dosage form) | OG5495 (mg/dosage form) |
|---|---|---|
| Hesperidin | 61.00 | 61.00 |
| Ellagic acid | 41.25 | 41.25 |
| Prune extract | 2.50 | 2.50 |
| Watercress extract | 2.50 | 2.50 |
| Chlorogenic acid | 55.71 | 55.71 |
| Cinnamon | 2.50 | 2.50 |
| Catechins | 8.58 | 8.58 |
| *Acacia nilotica* extract | 2.50 | 2.50 |
| Rosemary extract | 2.50 | 2.50 |
| *Momordica* extract | 2.57 | 2.57 |
| Grape seed extract | 12.50 | 12.50 |
| Artichoke extract | 2.50 | 2.50 |
| Blueberry extract | 10.00 | 10.00 |
| Ascorbic acid | | 66.39 |
| Ascorbyl palmitate | | 11.16 |
| Mixed carotenoids | | 28.86 |
| Vitamin A acetate | | 6.50 |
| Biotin | | 3.00 |
| Choline bitartrate | | 41.07 |
| Methylcobalamin | | 0.13 |
| Calcium L-mefolinate | | 0.56 |
| Lycopene | | 31.50 |
| Niacin | | 6.63 |
| Niacinamide | | 20.09 |
| D-calcium pantothenate | | 52.33 |
| Phytonadione Vitamin K | | 1.32 |
| Pyridoxine hydrochloride | | 17.97 |
| Riboflavin | | 8.94 |

TABLE 1-continued

| Ingredient | OG5507 (mg/dosage form) | OG5495 (mg/dosage form) |
|---|---|---|
| Thiamin mononitrate | | 15.80 |
| Vitamin D3 | | 7.00 |
| D-alpha mixed tocopheryl | | 157.14 |
| Chromium citrate | | 5.10 |
| Copper citrate | | 3.28 |
| Manganese citrate | | 1.16 |
| Magnesium citrate | | 127.50 |
| Molybdenum aspartate | | 25.50 |
| Potassium iodide | | 7.65 |
| Selenium aspartate | | 51.00 |
| Zinc citrate dihydrate | | 24.68 |
| Inositol | | 13.53 |
| Zeaxanthin | | 22.00 |
| Lutein | | 33.00 |

The evaluation of the effects of test compositions OG5495 and OG5507 on healthy and hydrogen peroxide treated Jurkat cells was performed by Trevigen Inc. (Gaithersburg, Md.) using their CometAssay® test system. The test procedures are summarized below Cell Treatment:

79 mg of OG5495 or 50 mg of OG5507 was suspended in DMSO. The compound solution was allowed to sit for 20 minutes at room temperature and vortex for 30 seconds every 5 minutes a. OG5495 was clarified (5000×g, 10 minutes) and transferred to a new tube. No additional clarification was necessary for OG5495. OG5507 required no clarification.

b. Starting compound concentration was 100 mg/ml. For OG5495, this was assumed based on information provided by inventors.

Note: Remaining steps were the same for both compounds. Compound treatment was performed on separate days.

A 20 mg/ml solution was prepared by combining 10 μl 100 mg/ml stock and 40 μl of DMSO.

$3 \times 10^5$ Jurkat cells in 3 ml of RPMI (no serum) were added to eight 15 ml conical tube. One tube for each group, for a total of 8 tubes. DMSO or compound was added to each tube (as described in table below). Cells were then incubated for 1 hour at 37° C. in a 5% CO2 incubator with lose caps to allow gas exchange

| | 3 ml of $3 \times 10^5$ cells | | | | |
|---|---|---|---|---|---|
| Sample | DMSO | 100 mg/ml | 20 mg/ml | 10 mM $H_2O_2$ | 2 mM $H_2O_2$ |
| DMSO Control | 3 ul | | | | |
| 20 μM $H_2O_2$ | 3 ul | | | 6 ul | |
| 2 μM $H_2O_2$ | 3 ul | | | | 3 ul |
| 100 μg/ml compound | | 3 ul | | | |
| 20 μM $H_2O_2$ + 100 μg/ml compound | | 3 ul | | 6 ul | |
| 20 μM $H_2O_2$ + 20 μg/ml compound | | | 3 ul | 6 ul | |
| 2 μM $H_2O_2$ + 100 μg/ml compound | | 3 ul | | | 3 ul |
| 2 μM $H_2O_2$ + 20 μg/ml compound | | | 3 ul | | 3 ul |
| | 1 hr at 37° C. in 5% CO2 | | | 20 minuts on ice | |

After 1 hour, samples were placed on ice. Hydrogen peroxide was added to appropriate tubes (as described in table above) and all samples were incubated on ice for 15 minutes.

1 ml of each sample was transferred to a 1.7 ml conical tube and cells were pelleted (250×g, 10 min, 4° C.). Total treatment time of 20 minutes in hydrogen peroxide.

After removing supernatant, cells were washed with 1 ml of cold 1×PBS and pelleted.

After removing the 1×PBS, cells were suspended in 1 ml freeze medium (80% RPMI, 20% FBS, 10% DMSO). A 50 µl sample aliquots were made. Samples were slowly frozen overnight at −80° C. before transferring to liquid nitrogen for storage.

Comet Assay:

1. 50 µl sample aliquots were quickly thawed and Alkaline Comet Control Cells (50 µl aliquots at 37° C.), transferred immediately to ice.
2. 500 µl of cold 1×PBS was added and spun @ 250×g for 5 min @ 4° C.
3. 525 µl of PBS was removed.
4. 50 µl of cold 1×PBS was added to pelleted cells.
5. 30 µl cells was added to 300 µl of molten LMagarose (37° C.).
6. 30 µl of LMagarose/Cell mixture per well was spread on 20 well slides. (Samples and controls are run in triplicate).
7. The slide was held @ 4° C. for 20 minutes.
8. Slides were transferred to Lysis Solution (pre-chilled to 4° C.) for 30 minutes at 4° C.
9. Slides were then transferred to Unwinding Solution (200 mM NaOH/1 mM EDTA) for 20 minutes at room temperature.
10. Slides were electrophoresed using Trevigen's Comet ES system using cold 200 mM NaOH/1 mM EDTA solution for 30 minutes at 21V.
11. Slides were then washed twice in water for 5 minutes at room temperature.
12. Slides were then washed in 70% Ethanol for 5 minutes at room temperature.
13. Dry slide on slide warmer (37-40° C.).
14. Add 50 µl/well of 1:30,000 SybrGold per well incubate for 30 minutes at room temperature in the dark.
15. Decant slide to remove SybrGold from slide.
16. Dip in water to quickly rinse.
17. Dry slide on slide warmer (37-40° C.).
18. Image using LOATS system Results:

OG5495:

At 100 µg/ml compound OG5495 appeared to induce DNA damage in Jurkat cells. This was demonstrated by an increase in tail moment and % DNA in the tail comparing DMSO and 100 µg/ml compound controls. Cells pretreated with 100 µg/ml OG5495 and exposed to 20 µM $H_2O_2$ showed a decrease in tail moment and % DNA in the tail relative to $H_2O_2$ alone.

OG5507:

At 100 µg/ml, compound OG5507 induced minimal damage; however, the % DNA in the tail is in the range where cells are considered healthy (less than 10% for % DNA in the tail). Unlike OG5495, OG5507 had a protective affect on Jurkat cells pretreated with 100 µg/ml of the compound before exposure to 20 µM $H_2O_2$. A dramatic decrease in both tail moment and % DNA in the tail was observed in cells pretreated with OG5507 compared to the untreated cells when exposed to 20 µM $H_2O_2$. A protective effect, although at a much lower level, was also seen in cells pretreated with 20 µg/ml of OG5507 compared to the untreated cells when exposed to 20 µM $H_2O_2$.

Figure 1:
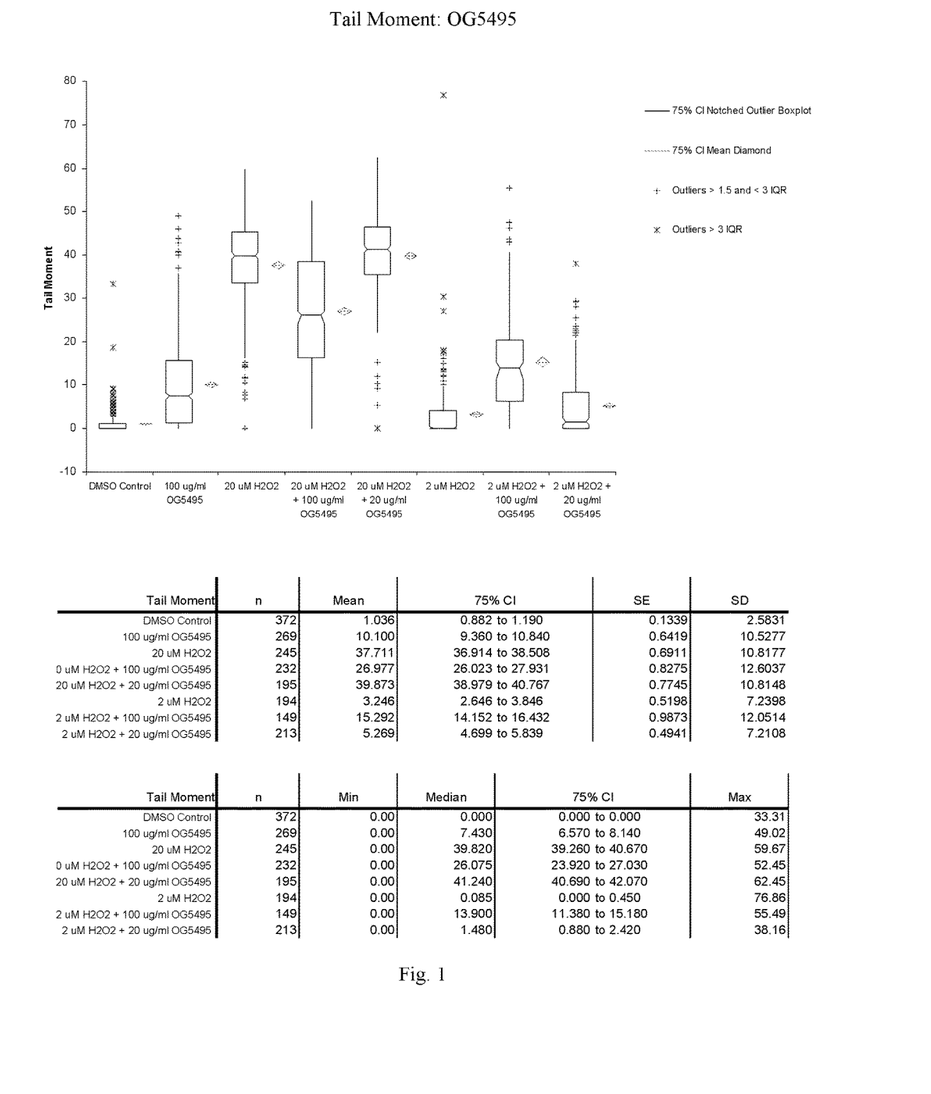
FIG. 1: A graphic representation of the Tail Moment for cells treated with OG5459 as measured in the Trevigen, Inc., CometAssay®.
Figure 2:
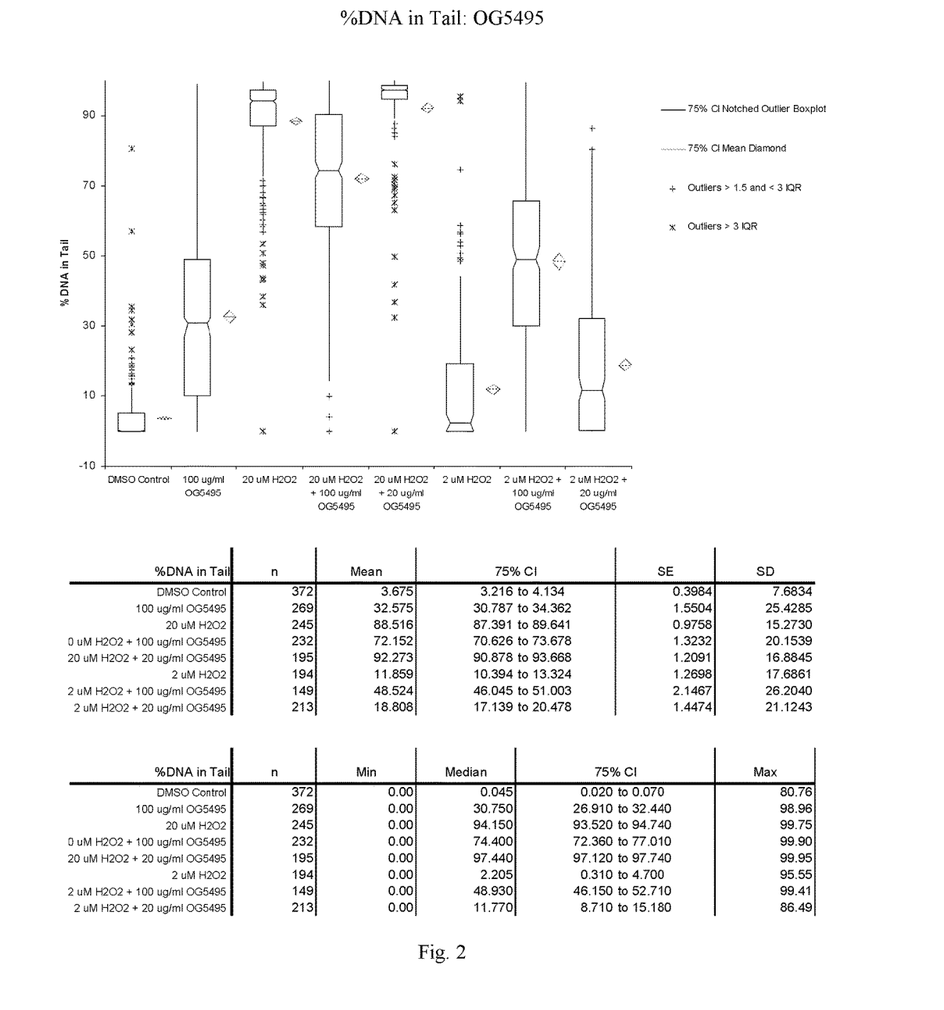
FIG. 2: A graphic representation of the % DNA in the tail for cells treated with OG5459 as measured in the Trevigen, Inc., CometAssay®.
Figure 3:
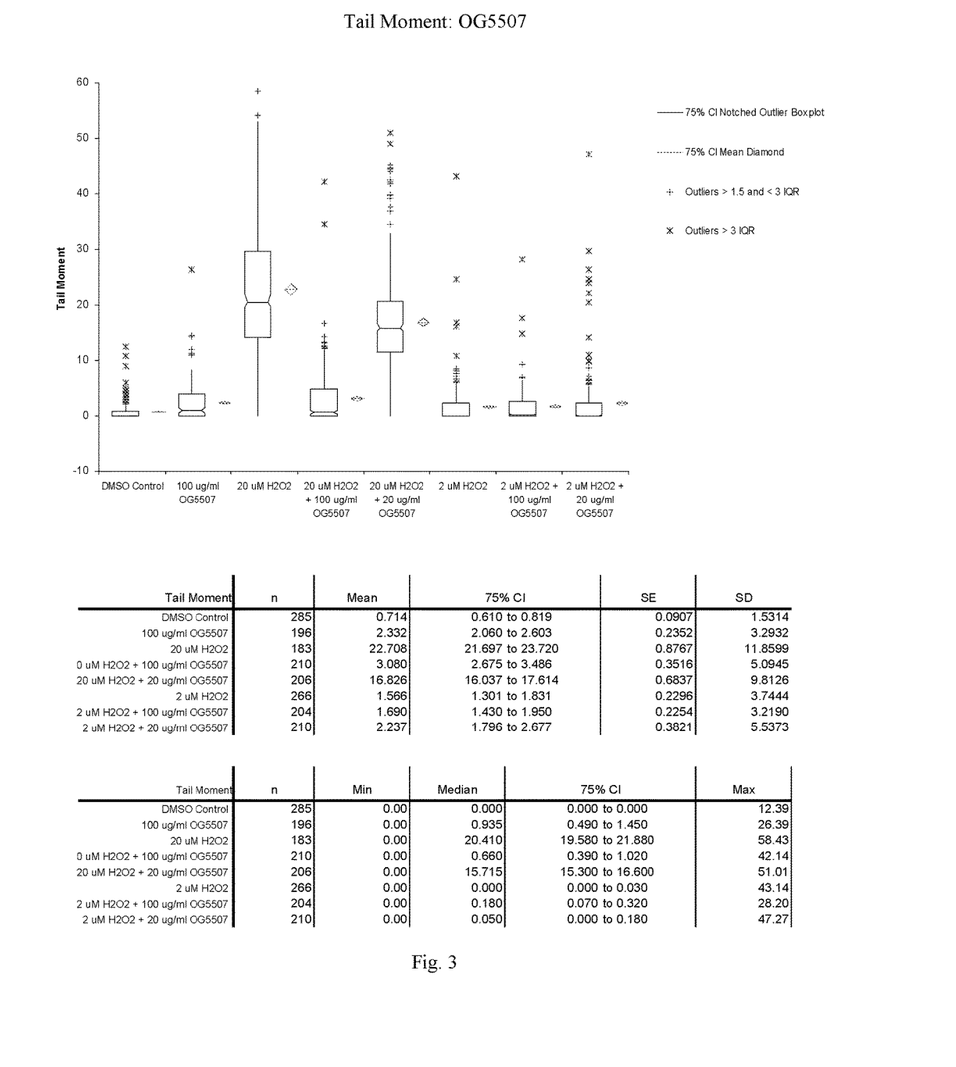
FIG. 3: A graphic representation of the Tail Moment for cells treated with OG5507 as measured in the Trevigen, Inc., CometAssay®.
Figure 4:
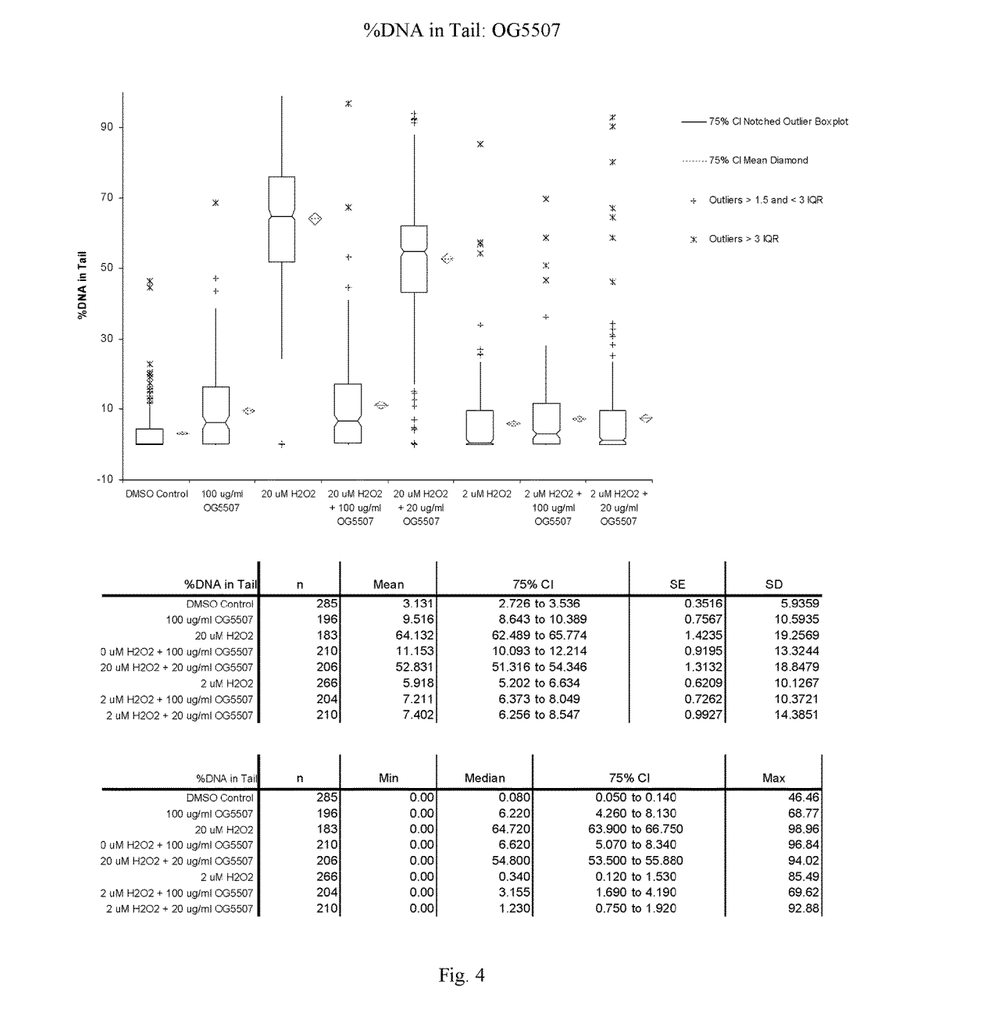
FIG. 4: A graphic representation of the % DNA in the tail for cells treated with OG5507 as measured in the Trevigen, Inc., CometAssay®.
Figure 5:
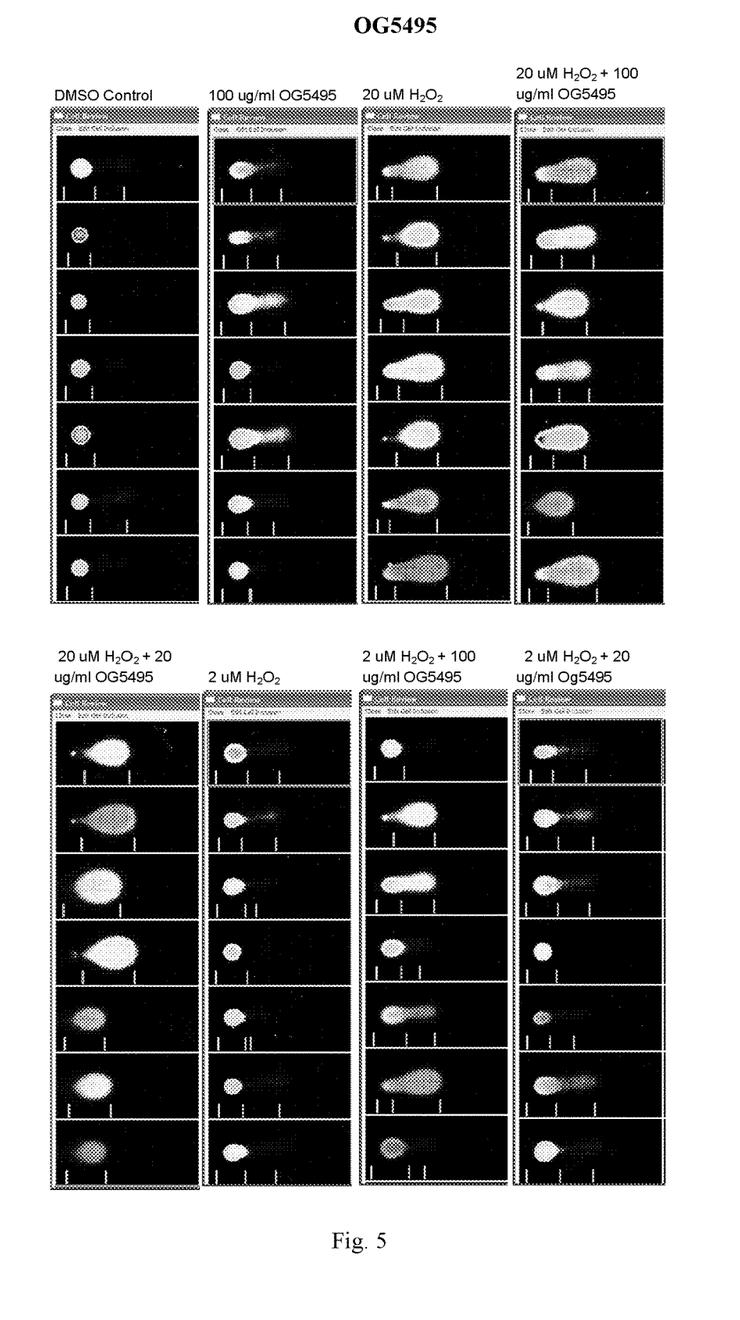
FIG. 5: Representative images for cells treated with OG5459 as measured in the Trevigen, Inc., CometAssay®.
Figure 6:
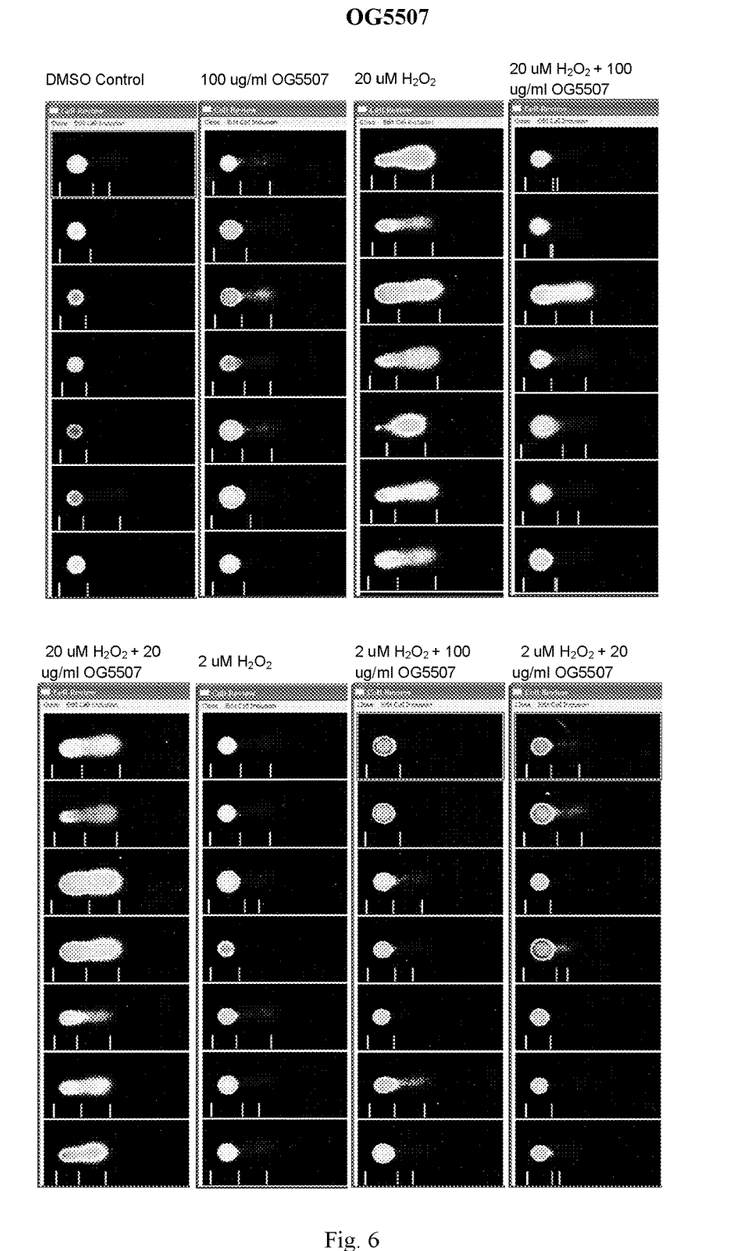
FIG. 6: Representative images for cells treated with OG5507 as measured in the Trevigen, Inc., CometAssay®.

The Tail Moment and % DNA in the tail are presented graphically for OG5495 in FIGS. 1 and 2 respectively and for OG5507 in FIGS. 3 and 4 respectively. Comet assay images for OG5495 and OG5507 are presented in FIGS. 5 and 6 respectively.

The results from this example are also summarized in Tables 2 and 3 below.

TABLE 2

OG5495: Mean Tail Moment and % DNA in Tail + Std Error

| Compound | Sample | Date Run | Comets Scored | Tail Moment | % DNA in Tail |
|---|---|---|---|---|---|
| OG5495 | DMSO Control | Oct. 24, 2011 | 372 | 1.04 ± 0.13 | 3.68 ± 0.40 |
| OG5495 | 100 µg/ml compound | Oct. 24, 2011 | 269 | 10.10 ± 0.64 | 32.58 ± 1.55 |
| OG5495 | 20 µM $H_2O_2$ | Oct. 24, 2011 | 245 | 37.71 ± 0.69 | 88.52 ± 0.98 |
| OG5495 | 20 µM H2O2 + 100 µg/ml compound | Oct. 24, 2011 | 232 | 26.98 ± 0.83 | 72.15 ± 1.32 |
| OG5495 | 20 µM H2O2 + 20 µg/ml compound | Oct. 24, 2011 | 195 | 39.87 ± 0.77 | 92.27 ± 1.21 |
| OG5495 | 2 µM $H_2O_2$ | Oct. 24, 2011 | 194 | 3.25 ± 0.52 | 11.86 ± 1.27 |
| OG5495 | 2 µM H2O2 + 100 µg/ml compound | Oct. 24, 2011 | 149 | 15.29 ± 0.99 | 48.52 ± 2.15 |
| OG5495 | 2 µM H2O2 + 20 µg/ml compound | Oct. 24, 2011 | 213 | 5.27 ± 0.49 | 18.81 ± 1.45 |

TABLE 3

OG5507: Mean Tail Moment and % DNA in Tail + Std Error

| Compound | Sample | Date Run | Comets Scored | Tail Moment | % DNA in Tail |
|---|---|---|---|---|---|
| OG5507 | DMSO Control | Nov. 1, 2011 | 285 | 0.71 ± 0.09 | 3.13 ± 0.35 |
| OG5507 | 100 µg/ml compound | Nov. 1, 2011 | 196 | 2.33 ± 0.24 | 9.52 ± 0.76 |
| OG5507 | 20 µM $H_2O_2$ | Nov. 1, 2011 | 183 | 22.71 ± 0.88 | 64.13 ± 1.42 |

TABLE 3-continued

OG5507: Mean Tail Moment and % DNA in Tail + Std Error

| Compound | Sample | Date Run | Comets Scored | Tail Moment | % DNA in Tail |
|---|---|---|---|---|---|
| OG5507 | 20 μM H2O2 + 100 μg/ml compound | Nov. 1, 2011 | 210 | 3.08 ± 0.35 | 11.15 ± 0.92 |
| OG5507 | 20 μM H2O2 + 20 μg/ml compound | Nov. 1, 2011 | 206 | 16.83 ± 0.68 | 52.83 ± 1.31 |
| OG5507 | 2 μM $H_2O_2$ | Nov. 1, 2011 | 266 | 1.57 ± 0.23 | 5.92 ± 0.62 |
| OG5507 | 2 μM H2O2 + 100 μg/ml compound | Nov. 1, 2011 | 204 | 1.69 ± 0.23 | 7.21 ± 0.73 |
| OG5507 | 2 μM H2O2 + 20 μg/ml compound | Nov. 1, 2011 | 210 | 2.24 ± 0.38 | 7.40 ± 0.99 |

Example 2

Effect of Phytonutrient Blend on ORAC Score

Purpose:

The purpose of this example was to determine the effects of a phytonutrient blend on Oxygen Radical Absorbance Capacity (ORAC).

Testing:

Tablets (1320 mg) from four (4) samples comprising 206.6 mg of a phytonutrient blend comprising:
  a. from 0.5 mg to 10 mg of *Acacia nilotica* extract;
  b. from 0.5 mg to 10 mg of artichoke extract;
  c. from 1 mg to 25 mg of blueberry extract;
  d. from 2.5 mg to 25 mg of catechins;
  e. from 25 mg to 75 mg of chlorogenic acid;
  f. from 0.5 mg to 10 mg of cinnamon;
  g. from 10 mg to 100 mg of ellagic acid;
  h. from 2.5 mg to 50 mg of grape seed extract;
  i. from 15 mg to 120 mg of hesperidin;
  j. from 0.5 mg to 10 mg of *Momordica* extract;
  k. from 0.5 mg to 10 mg of prune extract;
  l. from 0.5 mg to 10 mg of rosemary extract; and
  m. from 0.5 mg to 10 mg of watercress extract;
were tested by Brunswick Laboratories (200 Turnpike Rd, Southborough, Mass. 01772 USA) using their proprietary $ORAC_{FN}$ procedures. The total $ORAC_{FN}$ provides a measure of the total antioxidant power of a product against the five predominant reactive species. Results for test samples (foods) are reported as "trolox equivalents" or TEs.
were tested by Brunswick Laboratories (200 Turnpike Rd, Southborough, Mass. 01772 USA) using their proprietary $ORAC_{FN}$ procedures. The total $ORAC_{FN}$ provides a measure of the total antioxidant power of a product against the five predominant reactive species. Results for test samples (foods) are reported as "trolox equivalents" or TEs.

Results:

The results are presented below in Table 4 showing a strong antioxidant potential of the phytonutrient blend.

While the claimed invention has been described in detail and with reference to specific embodiments thereof, it will be apparent to one of ordinary skill in the art that various changes and modifications can be made to the claimed invention without departing from the spirit and scope thereof. Thus, for example, those skilled in the art will recognize, or be able to ascertain, using no more than routine experimentation, numerous equivalents to the specific substances and procedures described herein. Such equivalents are considered to be within the scope of this invention, and are covered by the following claims.

The invention claimed is:

1. A method for reducing or treating genetic damage induced by environmental agents in a mammal, wherein said method comprises administering a composition in a dosage form suitable for oral administration, said composition comprising a phytonutrient blend consisting essentially of:
  (a) *Acacia nilotica* extract;
  (b) artichoke extract;
  (c) blueberry extract;
  (d) catechins;
  (e) chlorogenic acid;
  (f) cinnamon;
  (g) ellagic acid;
  (h) grape seed extract;
  (i) hesperidin;
  (j) *Momordica* extract;
  (k) prune extract;
  (l) rosemary extract; and
  (m) watercress extract;
wherein in the phytonutrient blend: the *Acacia nilotica* extract (a) is present in an amount of from about 0.5 mg to 10 mg; the artichoke extract (b) is present in an amount of from about 0.5 mg to 10 mg; the blueberry extract (c) is present in an amount of from about 1 mg to 25 mg; the catechins (d) is present in an amount of from about 2.5 mg to 25 mg; the chlorogenic acid (e) is present in an amount of from about 25 mg to 75 mg; the cinnamon (f) is present in an amount of from about 0.5 mg to 10 mg; the ellagic acid

TABLE 4

ORAC Analysis of Phytonutrient Blend

| Sample # | Peroxyl Radicals (TE/g) | Hydroxyl Radicals (TE/g) | Peroxynittrite (TE/g) | Super Oxide Anion (TE/g) | Singlet Oxygen (TE/g) | Total ORAC/Tablet |
|---|---|---|---|---|---|---|
| 5507 | 1222 | 4754 | 119 | 3372 | 281 | 9,748 |
| 5790 | 1253 | 5074 | 114 | 1756 | 279 | 8,476 |
| 5792 | 1155 | 4954 | 111 | 1731 | 290 | 8,241 |
| 5861 | 1148 | 5586 | 120 | 1301 | 171 | 8,326 |

(g) is present in an amount of from about 10 mg to 100 mg; the grape seed extract (h) is present in an amount of from about 2.5 mg to 50 mg; the hesperidin (i) is present in an amount of from about 15 mg to 120 mg; the *Momordica* extract (j) is present in an amount of from about 0.5 mg to 10 mg; the prune extract (k) is present in an amount of from about 0.5 mg to 10 mg; the rosemary extract (l) is present in an amount of from about 0.5 mg to 10 mg; and the watercress extract (m) is present in an amount of from about 0.5 mg to 10 mg.

2. The method of claim 1, wherein the step of administering is defined as orally administering.

3. The method of claim 2, wherein the dosage form of the composition is selected from the group consisting of capsules, caplets, gelcaps, cachets, pills, and tablets.

4. The method of claim 3, wherein the dosage form is a tablet.

5. The method of claim 4, wherein the tablet is coated, and optionally scored.

6. The method of claim 2, wherein the dosage form of the composition is selected from the group consisting of solutions, suspensions, and emulsions.

7. The method of claim 2, wherein the dosage form of the composition is selected from the group consisting of elixirs, powders, lozenges, micronized particles, and osmotic delivery systems.

8. The method of claim 1, wherein the *Acacia nilotica* extract (a) is derived from gum resin, bark powder, or heartwood powder.

9. The method of claim 1, wherein the *Acacia nilotica* extract (a) is selected from acidic, alkaline, polar solvent, nonpolar solvent, or gastric fluid extracts.

10. The method of claim 1, wherein the composition is administered as a capsule, a caplet, a gel cap, a cachet, a pill, a tablet, a solution, a suspension, an oil-in-water emulsion, or a water-in-oil emulsion.

11. The method of claim 1, wherein the composition is administered prophylactically.

12. The method of claim 1, wherein the composition is administered palliatively.

13. The method of claim 1, wherein the mammal is a human.

14. The method of claim 1, wherein the composition further comprises a pharmaceutically acceptable vehicle.

15. The method of claim 14, wherein the pharmaceutically acceptable vehicle is selected from the group consisting of diluents and excipients.

16. The method of claim 1, wherein the composition further comprises one or more accessory ingredients.

17. The method of claim 16, wherein the accessory ingredient(s) is(are) selected from the group consisting of a binder, a lubricant, an inert diluent, a preservative, a surface active agent, and a dispersing agent.

18. The method of claim 1, wherein the phytonutrient blend consists of components (a) to (m).

* * * * *